Oct. 12, 1976
R. KORDES
ROSE PLANT
Filed Sept. 23, 1975
Plant Pat. 3,957
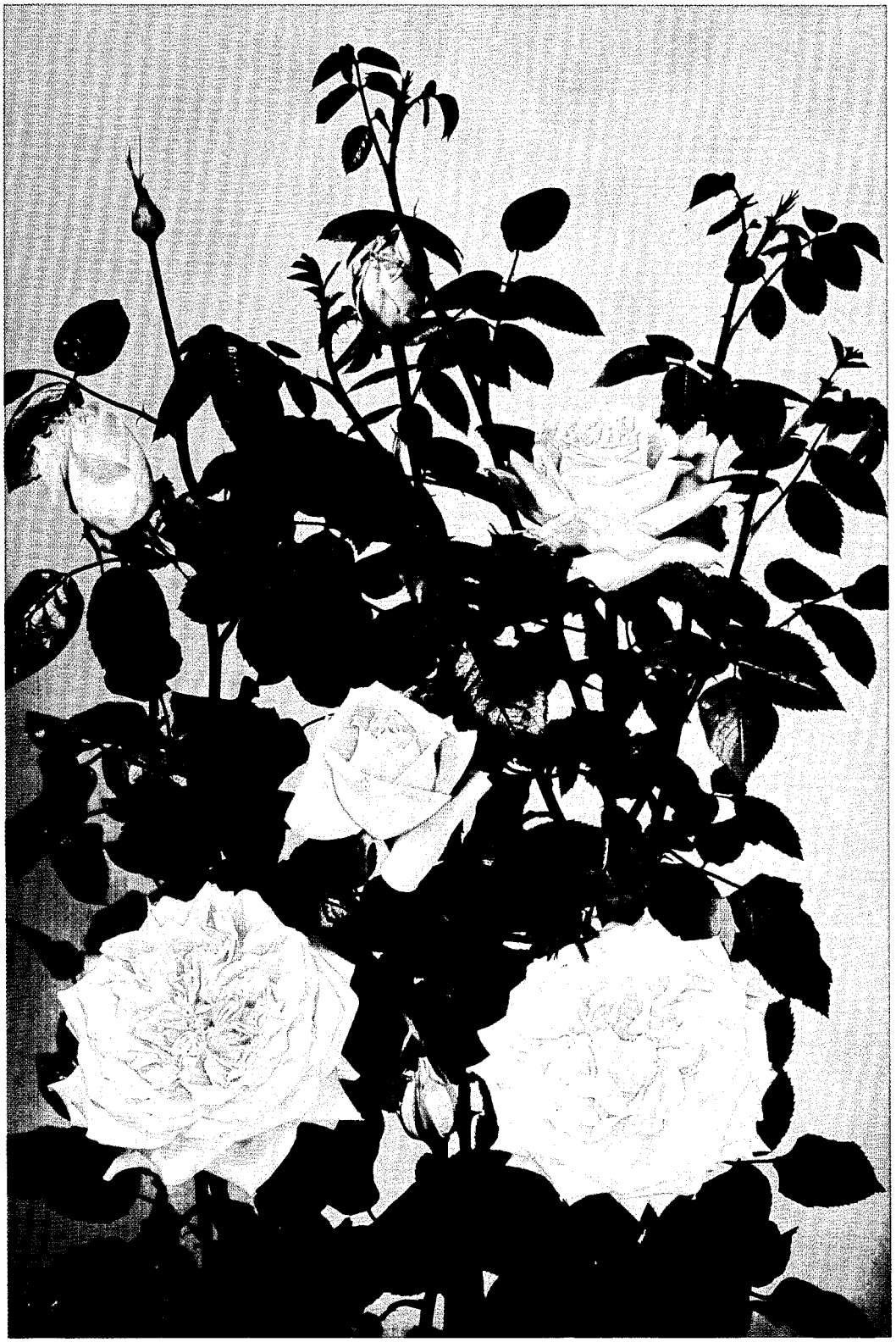

United States Patent

Plant Pat. 3,957

Patented Oct. 12, 1976

3,957

ROSE PLANT

Reimer Kordes, Aspern, Germany, assignor to Armstrong Nurseries, Inc., Ontario, Calif.

Filed Sept. 23, 1975, Ser. No. 615,981

Int. Cl.[2] A01H 5/00

U.S. Cl. Plt.—11 1 Claim

ABSTRACT OF THE DISCLOSURE

An asexually reproduced hybrid tea rose plant of the outdoor bush type, grown mainly for garden decoration. The plant is of upright bushy form, many-branched, and of vigorous growth habit. An important characteristic is its more than average resistance to mildew, as compared to similar varieties grown under comparable conditions. There is a notable difference in the shade and color of the flower petals, from red-tipped golden buds through dual-color fully-opened flowers, which are golden without and apricot (blushed red when grown outdoors) within. The petalage is distinctly double, and the flowering habit is almost continuous throughout the growing season. The styles and the stamen-filaments are devoid of visible red pigments.

This invention relates to a new type of hybrid tea rose. The plant is a seedling of the bushy outdoor type, cultivated for garden decoration. It was asexually reproduced by Reimer Kordes in Sparrieshoop, Holstein, Germany, having as its seed parent "Colour Wonder" (also known as "Königin der Rosen") and, as its pollen parent, "King's Ransom." It holds its distinguishing characteristics through succeeding propagations by budding.

The plants shown in the drawings and described in this specification were grown in winter in a greenhouse in southern California, but the bush characteristics described herein pertain as well to plants grown out of doors in southern California, except as noted.

The new variety bears its flowers usually singly on strong medium-length stems, but sometimes may bear several flowers to a stem. The plant blooms freely outdoors, and nearly continuously during the growing season. The blooms have a slight tea fragrance.

The new cultivar may be distinguished from its seed parent, Colour Wonder, in several ways, such as the fact that "Modern Roses 7" attributes 50 petals to Colour Wonder, whereas this new variety has from 65 to 75 petals plus many petaloids. Furthermore, Colour Wonder tends to bloom only intermittently, whereas the new cultivar blooms freely and almost continuously throughout the growing season. Furthermore, the new cultivar gives a significantly greater yield of blooms than its seed parent.

The seed parent, furthermore, has many large and small prickles on its stems and branches, while this new rose, although it has both large and small prickles on its main stems, including several large prickes, has significantly fewer prickles both large and small than Colour Wonder.

A striking difference between the pollen parent and the new cultivar is in the coloration of the flower petals. The new rose has an orange-coral color, with golden yellow on the reverse side of the petals. King's Ransom, on the other hand, is clear golden yellow in color, according to "Modern Roses 7." Furthermore, whereas King's Ransom has from 35 to 40 petals, this new cultivar, as mentioned above, has from 65 to 75 petals plus many petaloids. In other words, the new cultivar has significantly more petals in its bloom than either of its parents.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designates values based upon the Nickerson Color Fan, put out by Munsell Color Co.

BUD

The peduncle is short to average in length and of average to heavy caliper, being erect and stiff, and with numerous stipitate glands. The color is between Moderate Yellow Green, 5GY5/6, and Moderate Olive Green, 5GY4/3.

Before the calyx breaks, the bud is small in size, medium length, of pointed, ovoid form, and with foliaceous appendages and stipitate glands on the surface of the bud, the foliaceous parts extending beyond the tip of the bud a distance equal to one-half or more of its length.

As the calyx breaks, the color is near Brilliant Yellow, 5Y9/9. The inner surface of the sepals carries a fine wooly tomentum, while the outer surface contains stipitate glands.

As the first petal opens, the bud is average in size, of medium length, and ovoid. The color on the outside of the petal is near Vivid Yellow, 2.5Y8/12. The inside surface of the petal is between Strong Orange, 5YR7/11, and Strong Yellowish Pink, 10R7/9. The bud opens up well, and is not retarded from opening by cold, hot, wet, or dry weather.

In southern California, this cultivar often tends to have a "confused center," or a vegetative center, when grown outdoors.

BLOOM

The description which follows is of flowers grown in a greenhouse in January in southern California.

The size of the bloom when fully open is from average to large, ranging from 4½ to 5 inches. The petalage is double to very double, with from 65 to 75 petals arranged in regular imbrication or in quarters, plus 20 to 50 petaloids.

The bloom is full and high centered at first, becoming open and full. At first the petals remain somewhat cupped, with tips reflexed outward, becoming later at maturity more loosely cupped, with tips reflexed outward. The form of the bloom varies from well-imbricated to irregular.

The petals are of medium thickness, moderately leathery, with inside slightly shiny to satiny, and on the outside shiny to satiny. The outside petals are broadly obovate, as are also the intermediate petals. The inside petals are obovate to irregular. The bases of the petals elongate as the flowers age. The colors may be modified by being striped, blotched, shaded and/or washed or tinted with other colors.

The paragraphs immediately following describe color values observed in a flower newly opened in the month of January. The plant had been grown in a greenhouse, in Ontario, Calif.

The outer surface of the outside petal is near Brilliant Greenish Yellow, 10Y9/9, with some irregular vegetative streaks and blotches. The inner surface of the outside petal is between Brilliant Greenish Yellow, 7.5Y9/8, and Brilliant Yellow, 5Y9/9, in the lower or basal third of the petal, while the remainder is between Moderate Yellowish Pink, 10R8/6, and Moderate Yellowish Pink, 7.5R8/6, generally blotched with lighter colors and vegetative streaks.

The outer surface of the intermediate petal smoothly blends from near Brilliant Yellow, 5Y9/9, at the base, to near Pale Orange Yellow, 7.5YR9/4, along the margins. The inner surface of the intermediate petal is near Vivid Yellow, 5Y8/12, in the basal fourth of the petal, blending to near Moderate Yellowish Pink, 10R8/6, at the apical margin.

The outer surface of the inside petal smoothly blends from near Vivid Yellow, 5Y8/12, at the base to near Moderate Orange Yellow, 7.5YR8/8, along the margins. The inner surface is near Vivid Yellow, 5Y8/12, in the basal quarter of the petal, blending to a color near Strong Yellowish Pink, 10R7/9, at the margins.

The paragraphs immediately following describe the color values observed in a bloom which had been open for three days, in a greenhouse, in the month of January. The plant was grown in Ontario, Calif.

The outer surface of the outside petal is near Brilliant Yellow Green, 2.5GY9/8, with some vegetative streaks running irregularly through the petal. The inner surface of the outside petal is near Brilliant Greenish Yellow, 7.5Y9/8, in the basal quarter of the petal, while the remainder is between Moderate Yellowish Pink, 7.5R8/6, and Moderate Pink, 5R8/6, usually with vegetative streaks running irregularly through the petal.

The outer surface of the inside petal is between Brilliant Greenish Yellow, 7.5Y9/8, and Brilliant Yellow, 5Y9/9, generally becoming lighter toward the margins. The inner surface of the inside petal is near Brilliant Greenish Yellow, 7.5Y9/8, in the basal fourth of the petal, while the remainder is between Light Orange, 2.5YR8/6, and Moderate Yellowish Pink, 10R8/6.

The general color effect of the newly opened flower (grown in the greenhouse) is between Light Orange, 2.5YR8/6, and Moderate Yellowish Pink, 7.5R8/6. The bloom after being three days open gives a general color effect which is between Light Orange, 2.5YR8/6, and Moderate Yellowish Pink, 7.5R8/6. The petals usually drop off cleanly, except for petaloids, and are not particularly affected by cold, hot, wet, or dry weather.

The flower on the bush in the garden persists for about 5 days in the month of October, in southern California. Cut roses grown in the greenhouse and kept at living-room temperatures will last from 4 to 5 days in the month of January.

REPRODUCTIVE ORGANS

Stamens: The stamens are from average to few in number, arranged regularly about the pistils, while many become petaloids as the flowers age.

Filaments: The filaments are of medium length, being 5–7 cm. in length, and near Vivid Yellow, 2.5Y8/12, in the newly opened flowers. No red pigment is visible on any filaments. There are a few viable anthers.

Anthers: The anthers are from small to medium in size, all opening approximately at once. Along the margins on the upper side the color is near Strong Orange Yellow, 7.5YR7/11, while the mid-portion of the upper side and the under side is near Brilliant Yellow, 2.5Y9/9.

Pollen: Pollen is somewhat sparse to moderate, and near Strong Orange Yellow, 7.5YR7/11, in color.

Pistils: The pistils are approximately 140 in number, this being from average to many.

Styles: The styles are uneven, average in caliper, and near Brilliant Greenish ellow, 7.5Y9/8, in color. They are devoid of visible red pigments.

Stigma: The stigma is near Brilliant Greenish Yellow, 7.5Y9/8, in color.

Ovaries: The ovaries are enclosed in the calyx, when viable, but often becoming vegetative with age and protruding from the calyx.

Hips: Hips are average length, and flat to globular. At the half-mature stage, the color is between Strong Yellow Green, 2.5GY6/8, and Strong Yellow Green, 5GY6/8. The walls are smooth, thick and fleshy.

This cultivar does not set hips naturally when cultivated outdoors in southern California. When pollinated under controlled conditions, in a greenhouse, this cultivar does set some hips, but is only partially fertile.

Sepals: The sepals were manually removed from the hips when pollinated, so there were none available for description.

Seeds: Seeds are few in number, from one to ten, and are of medium size.

FOLIAGE

The compound leaves usually comprise three to seven leaflets. They are abundant, medium size, heavy, somewhat leathery, and glossy. The leaflets are ovate, with apex acute to mucronate, and margin doubly serrate.

The mature foliage displays upon its upper surface a color which is near Moderate Olive Green, 2.5GY4/3. The under surface is a grayish olive green: No color on the Munsell Color Fan approximates or even comes close to this color.

The young foliage on its upper surface is near Moderate Yellow Green, 5GY5/6, strongly overlaid with near Dark Red, 5R3/7, while the under surface is near Dark Red, 5R3/7.

The rachis is average to heavy in size, grooved on its upper side, with many stipitate glands on the edges. The under side is sparsely prickly, and has stipitate glands.

The stipules are medium-length to long, narrow, and with medium-length points turning out at an angle of 45° or less.

The plant displays a more than average resistance to mildew, when compared to other varieties in commerce, grown under similar conditions, in southern California.

GROWTH

The habit of growth of the plant is bushy, upright, and much branched. It displays a very vigorous growth. The canes are medium to heavy in caliper.

The main stems are near Light Olive, 10Y5/5, in color. They bear several medium-length large prickles which are hooked slightly downward, are moderately broad at the base and are Strong Yellowish Brown, 7.5YR5/7, to gray, in color. There are few small prickles, which are the same coloration as the large prickles. There are no hairs.

The branches are near Moderate Yellow Green, 2.5GY5/5, in color. They bear few to several medium-length large prickles, which are hooked slightly downward, with medium-length moderately broad base, and a color which is near Strong Brown, 5YR4/5. There are few small prickles, which are the same coloration as the large prickles. There are no hairs.

New shoots are near Moderate Yellow Green, 5GY5/6, in color, strongly overlaid with near Dark Red, 5R3/7. There are few large prickles, which are medium-length, hooked slightly downward, with medium-length moderately narrow base. Their color is near Moderate Yellow Green, 5GY5/6, strongly overlaid with near Dark Red, 5R3/7. There are a few small prickles, which are the same color as the large prickles. There are no hairs, but many stipitate glands.

As noted above, roses of this new variety, when grown outdoors do sometimes develop confused or "vegetative" centers. Furthermore, as also noted above, roses of this new variety do not set hips when grown outdoors, and only irregularly develop hips when grown in the greenhouse. The color of flowers grown outdoors tends to be more intense than on greenhouse-grown flowers, but in the same hues with the additional overlay of a color near Vivid Red, 5R5/13, where exposed to direct sunlight. Except in these respects, no significant difference has been noted whether the plants were grown indoors or outdoors.

Although the color of the flowers of this cultivar is much more intense, and is highly distinctive, when well-grown outdoors, specially in a cool climate, it may be desirable to grow it in the green house in certain areas. In Ontario, Calif., for example, the blooms on garden-grown plants occasionally develop vegetative centers in which the characteristic brilliance of coloration is diminished. In much of the rest of this country, however, the overall color of the blooms on plants grown outdoors is a rich peachy orange sometimes lightly flushed with red, and having a golden-yellow reverse.

I claim.

1. An asexually reproduced hybrid tea rose plant of the outdoor bush type, substantially as shown and described herein, which blooms freely throughout the season and has a sturdy habit of growth, stiff erect peduncles having numerous stipitate glands, having several large and a few small prickles on stems and branches, and possessing glossy foliage which is relatively more resistive to mildew than comparable varieties grown under equivalent conditions; the plant being especially characterized by the coloration of its bloom, with flower petals ranging from golden yellow tipped with red in the bud stage, opening to double-shaded petals golden without and apricot within, the inner faces of petals often being blushed red when the plant is grown outdoors, and at the end of blooming manifesting a lighter shade of the same coloration; the bloom also being characterized as to its configuration by the presence of 65 to 75 petals with 20 to 50 petaloids, and also 140 pistils, and styles and stamen-filaments being devoid of visible red pigments.

No references cited.

ROBERT E. BAGWILL, Primary Examiner.